(12) United States Patent
Allan

(10) Patent No.: US 8,463,560 B2
(45) Date of Patent: Jun. 11, 2013

(54) METHOD AND APPARATUS FOR MEASURING PROPERTIES OF BOARD PRODUCTS

(75) Inventor: Russell John Allan, North Croydon (AU)

(73) Assignee: Testing Machines, Inc., New Castle, DE (US)

( * ) Notice: Subject to any disclaimer, the term of this patent is extended or adjusted under 35 U.S.C. 154(b) by 1154 days.

(21) Appl. No.: 11/992,021

(22) PCT Filed: Sep. 19, 2006

(86) PCT No.: PCT/AU2006/001370
§ 371 (c)(1),
(2), (4) Date: Mar. 13, 2008

(87) PCT Pub. No.: WO2007/033410
PCT Pub. Date: Mar. 29, 2007

(65) Prior Publication Data
US 2010/0161253 A1     Jun. 24, 2010

(30) Foreign Application Priority Data
Sep. 21, 2005   (AU) .............................. 2005905216

(51) Int. Cl.
G01B 5/28     (2006.01)
G01H 1/00     (2006.01)
D21F 7/06     (2006.01)

(52) U.S. Cl.
USPC ............................. 702/39; 73/579; 162/263

(58) Field of Classification Search
USPC ........... 702/39, 33–36, 42, 48, 56–57, 64–67, 702/75–76, 79, 81, 84, 127, 159, 171, 182–183, 185, 189; 73/1.82, 1.89, 159, 570, 573, 579, 73/584, 588–589, 597–598, 632, 645–646, 73/649; 162/49, 198, 263
See application file for complete search history.

(56) References Cited

U.S. PATENT DOCUMENTS

| | | | |
|---|---|---|---|
| 4,291,577 A | 9/1981 | Baum et al. | 73/597 |
| 4,688,423 A * | 8/1987 | Orkosalo | 73/159 |

(Continued)

FOREIGN PATENT DOCUMENTS

| | | |
|---|---|---|
| GB | 2369186 | 5/2002 |
| SU | 566152 | 7/1977 |

(Continued)

OTHER PUBLICATIONS

Vun et al., Ultrasonic Characterization of Structural Properties of Oriented Strandboard: A Comparison of Direct-Contact and Non-Contact Methods, 2003, Wood and Fiber Science, pp. 381-396.*

(Continued)

*Primary Examiner* — Toan Le
(74) *Attorney, Agent, or Firm* — Harrity & Harrity, LLP

(57) ABSTRACT

An apparatus and method device for measuring at least one property of a board product, such as a paperboard product which includes a transmitter for applying a vibrational excitation to at least one region of the board product. The excitation includes a plurality of frequencies lying within a predetermined frequency range. The apparatus further includes a receiver for measuring a vibrational response of the board product to the vibrational excitation. A processor processes the measured vibrational response to obtain a frequency response of the region of the board product to the excitation, and analyzes the frequency response to determine a measure of at least one property of the board product.

27 Claims, 9 Drawing Sheets

U.S. PATENT DOCUMENTS

| | | | |
|---|---|---|---|
| 4,713,572 A | 12/1987 | Bokowski et al. | 310/323.01 |
| 4,730,492 A | 3/1988 | Burk | 73/597 |
| 4,735,087 A | 4/1988 | Hourani et al. | 73/597 |
| 4,864,851 A | 9/1989 | Haughton | 73/159 |
| 4,936,141 A | 6/1990 | Anderson, Jr. et al. | 73/159 |
| 4,958,522 A | 9/1990 | McKinlay | 73/847 |
| 4,970,895 A | 11/1990 | Houghton et al. | 73/159 |
| 4,991,432 A | 2/1991 | Houghton et al. | 73/159 |
| 5,013,403 A | 5/1991 | Chase | 162/49 |
| 5,101,661 A | 4/1992 | Cresson et al. | 73/159 |
| 5,104,488 A | 4/1992 | Chase | 162/198 |
| 5,138,878 A | 8/1992 | Cresson et al. | 73/159 |
| 5,398,538 A | 3/1995 | Williams et al. | 73/1.37 |
| 5,479,825 A | 1/1996 | Williams et al. | 73/644 |
| 5,621,172 A | 4/1997 | Wilson et al. | 73/579 |
| 5,672,828 A * | 9/1997 | Allan | 73/579 |
| 5,808,199 A * | 9/1998 | Kazys et al. | 73/597 |
| 5,824,908 A | 10/1998 | Schindel et al. | 73/632 |
| 5,847,281 A * | 12/1998 | Kazys et al. | 73/597 |
| 6,810,741 B1 | 11/2004 | Lafleur et al. | 73/571 |
| 2003/0136199 A1 | 7/2003 | Singleton et al. | 73/846 |

FOREIGN PATENT DOCUMENTS

| | | |
|---|---|---|
| WO | 9115764 | 10/1991 |
| WO | WO 95/11453 | 4/1995 |
| WO | WO 01/09603 | 2/2001 |

OTHER PUBLICATIONS

Kazys et al., Ultrasonic Non-Destructive On-Line Estimation of the Tensile Stiffness of a Running Paper Web, 2001, NDT&E International 34, pp. 259-267.*

Habeger et al., Ultrasonic Velocity Measurements in the Thickness Direction of Paper, 1986, Journal of Applied Polymer Science, vol. 32, pp. 4503-4540.*

Baum et al., On-Line Measurement of Paper Mechanical Properties, Jan. 1980, IPC Technical Paper Series, No. 91, The Institute of Paper Chemistry, Appleton, Wisconsin, 17 pp.*

International Search Report and Written Opinion of the International Searching Authority corresponding to PCT/AU2006/001370 mailed Oct. 20, 2006, 7 pages.

* cited by examiner

METHOD AND APPARATUS FOR MEASURING PROPERTIES OF BOARD PRODUCTS

FIELD OF THE INVENTION

The present invention relates generally to the measurement of properties of board products, such as corrugated paperboard and the like, and more particularly to an improved method and apparatus for measurement of structural and strength properties of board products during manufacture. The inventive method and apparatus may be useful for performing continuous on-line measurement of board properties during manufacture, and may be adapted to provide a means for portable, non-destructive testing of board products.

BACKGROUND OF THE INVENTION

In the manufacture of board products, and particularly paperboard products such as corrugated paperboard, it is desirable to measure various properties of the paperboard product during manufacture, for example for the purposes of quality control. It is especially useful to measure "damage" or degradation, which may occur during manufacture of paperboard. It is generally accepted that degradation may usefully be assessed by measuring the strength of the finished board products.

Shear stiffness, and in particularly machine direction (MD) shear, is one property that provides an indication of paperboard performance.

One known method for measuring shear stiffness is by a twisting test, as disclosed in U.S. Pat. No. 4,958,522. However, this method has a number of disadvantages. Firstly, it requires that samples be prepared for testing, which must be accurately cut to size from the manufactured paperboard. The test apparatus is relatively bulky, complex and expensive. Furthermore, since it operates upon cut samples, the twisting test is a destructive test that cannot be used for continuous on-line measurement of board products during manufacture. The lack of a practical continuous measurement method results in uncertainty in the strength of manufactured board products, and accordingly it has become the usual practice to manufacture board products using heavier grade materials in order to provide a sufficient strength margin to compensate for this uncertainty.

It is therefore considered desirable to provide a method of assessing relevant properties of paperboard that may be employed on-line during manufacture, or for non-destructive random or spot testing of manufactured board products, for purposes of quality control, thereby enabling the use of cheaper, lighter grade materials, due to a reduced need to allow for a strength margin in the finished board products.

A non-destructive test method and apparatus is disclosed in international publication no. WO 01/53828 (equivalent to US publication no. 2003/0136199). The apparatus and method disclosed therein have the advantage that the sample to be tested does not need to be cut, thereby reducing or eliminating the preparation time. A predetermined force is applied to a corrugated board product, such that the board is not deflected beyond an elastic region. According to the disclosure, the force is applied via a plunger, and the deflection is limited by a self-limiting apparatus ensuring that the board remains exercised within its elastic limit. The resulting force-displacement characteristic is used to provide indicative results of MD shear by calculating the gradient of the curve within the elastic region.

However, the disclosure of WO 01/53828 admits at least the following problems with the elastic deflection method. A discrepancy was identified between MD shear and the force-displacement characteristic depending upon the board grade. It is therefore necessary to calibrate the apparatus according to differing grades of board being measured, since the measurement result is dependent upon the weight of materials, and not solely upon intrinsic characteristics of the paperboard. Additionally, results show a strong dependency on the velocity of the moving board when on-line measurements are performed. This requires the measured results to be corrected according to a logarithmic relationship. Overall, therefore, the elastic deflection method requires additional information to be determined both prior to and during the measurement, in order to ensure that appropriate corrections are made to the measured result.

A need therefore remains for an improved method and apparatus for measuring the properties of board products, which is compatible with performing continuous non-destructive on-line measurement, and which can provide at least a useful alternative to prior art measurement techniques, preferably also mitigating the aforementioned known problems in the art. It would also be desirable to provide a compact, portable, apparatus for testing of board products, which may be employed for quality control purposes, such as in random or spot testing of manufactured products.

It will be appreciated that the foregoing discussion is provided to explain the context of the invention, and should not be taken as an admission that any of this material formed part of the prior art base, or of the common general knowledge, in the relevant art on or before the priority date of any of the statements herein, or any claims appended hereto.

SUMMARY OF THE INVENTION

In one aspect, the present invention provides a method of measuring at least one property of a board product, such as a paperboard product, including the steps of:

applying a vibrational excitation to at least one region of the board product, the excitation including a plurality of frequencies lying within a predetermined frequency range;

measuring a frequency response of said region of the board product to the excitation; and analysing the frequency response to obtain a measure of at least one property of the board product.

Advantageously, a method according to the invention may be adapted for on-line use, so as to continuously monitor and indicate a level of damage occurring to a board product, including paperboard products such as corrugated paperboard, which is non-destructive of the board under test. Real-time feedback may thereby be provided, allowing for machine-operated and/or automated systems to perform quality control functions during manufacture, in order to minimise product variability, and maximise product strength and quality. It may thereby be possible to avoid the practice of using more costly heavier grade materials than necessary, due to the reduced uncertainty in the strength of the manufactured board products. Alternatively, the method may be adapted for deployment within a compact, portable test apparatus, which may be useful for random or spot testing of manufactured board products.

The present inventive method of measuring properties of board products may enable a number of further advantages to be realised as compared with known methods. In some embodiments, a non-contact measurement is possible, thereby minimising the potential of the measurement apparatus to cause any degradation in the quality or strength of the board product under test. Avoiding contact with the board product also minimises wear, and corresponding maintenance costs, of the measurement apparatus. Other potential advantages include the ability to test much larger, and therefore more representative, samples of the manufactured board products, the possibility of performing measurements that reflect intrinsic properties of the board product without the need to correct for board weight, geometry, velocity and the like, and the potential for automation of the complete measurement.

Preferably, the predetermined frequency range of the vibrational excitation includes a range of acoustic frequencies. In preferred embodiments of the method, frequencies between 50 Hz and 400 Hz are utilised, it being particularly preferred that frequencies within the range of 100 Hz to 300 Hz are utilised.

In some embodiments of the method, the vibrational excitation may be applied in the form of a swept or stepped vibrational frequency within the predetermined frequency range. In alternative embodiments, a vibrational excitation may be applied which simultaneously includes a plurality of frequencies lying within the predetermined frequency range, such as a white noise type excitation.

The measure of said at least one property of the board product is preferably a resonance peak frequency of the measured frequency response within the predetermined frequency range. In a preferred embodiment, the resonance peak frequency is scaled to provide a measure of board quality. It is particularly preferred, though not essential, that the scale factor be selected to correspond with the type of board product under test in order to provide a quality measure that may be compared across different types of board product.

The property obtained from said measure may be an MD shear value, corresponding with values obtained using a known twisting test, or alternatively may be a shear stiffness or shear modulus value. Advantageously, the method may thereby enable an absolute measurement of an intrinsic property of the board product, such as shear stiffness, to be obtained.

Alternatively, some embodiments of the method may provide a relative, rather than absolute measurement of a property of the board product, providing an indication of changes in said property over time and/or location on the board product, such as a continuous measurement of variation in the property during on-line measurement in the course of manufacture of a board product. Such relative variations in the value of the measure of the property may be indicative of damage or other degradation in quality of the manufactured board product. For example, a change in the resonance peak frequency of the frequency response, or a corresponding board quality measure, may be indicative of corresponding damage or degradation of the board product.

In one particular approach, the finished board product includes a plurality of components assembled to form a multilayer product, and the method includes estimating a strength of each component of the board product prior to manufacture, determining an expected value of a property of the board product based upon said strength estimates, and comparing the expected value with the measured value of the property of the finished board product in order to detect damage or degradation of the product during manufacture.

In another aspect the invention provides an apparatus for measuring at least one property of a board product, such as a paperboard product, the apparatus including:

a transmitter arranged to apply a vibrational excitation to at least one region of the board product, said excitation including a plurality of frequencies lying within a predetermined frequency range;

a receiver arranged to measure a vibrational response of the board product to the vibrational excitation; and a processor configured to process the measured vibrational response to obtain a frequency response of said region of the board product to said excitation, and to analyse the frequency response to determine a measure of at least one property of the board product.

The transmitter preferably includes a transmitting transducer, such as an electromechanical transducer, which converts an input electrical signal into a corresponding vibrational excitation signal. Advantageously, the direction of vibration is selected to exercise a desired structural characteristic of the board product, and in particular, for example, a vibrational excitation along the machine direction may be applied to facilitate the measurement of MD shear, or shear stiffness in the machine direction. However, the structural characteristics of interest may be excited in embodiments of the invention by a variety of different vibrational excitations.

In some embodiments the transmitter may be a non-contacting transmitter. For example, the transmitter may apply a vibrational excitation to the board product utilising sound waves. In an exemplary embodiment of this type, the transmitting transducer includes a speaker and associated driving electronics, the output of the speaker being directed towards the said region of the board product.

In other embodiments, the transmitter may be a contacting transmitter. In exemplary embodiments of this type, the transmitter includes a transmitting contactor, such as a contact wheel for on-line measurement of moving paperboard, or a stationary contactor for measurement of properties of a cut sheet or stationary sheet. An appropriate load pressure is preferably selected such that vibrational excitations are transferred into the board under test without causing significant flexing or displacement of the board product.

In embodiments including a contacting transmitter, the transmitting transducer may include an actuator, which applies vibrational energy to the contactor. For example, a piezo-electric actuator is suitable for this purpose.

The receiver preferably includes a receiving transducer, such as an electro-mechanical transducer which converts received vibrational, energy into a corresponding output electrical signal.

In some embodiments of the invention, a non-contacting receiver may be provided, which may, for example, receive soundwaves emitted from the said region of the board product. In one exemplary embodiment of this type, the receiver includes a microphone, such as a directional microphone directed towards the said region of the board product.

In other embodiments, a contacting receiver may be provided. In such embodiments, the receiver preferably includes a receiving contactor, such as a contact wheel for use in on-line measurement of properties of moving board products, or a stationary contactor for performing measurements of cut sheets, or stationary sheets. The contacting receiver preferably further includes a receiving transducer including a vibration sensor. Suitable vibration sensors include piezo-electric type sensors for directly or indirectly measuring the vibrational energy of the board product. In this regard, a variety of sensor types, including displacement sensors and/or accelerometers, may be utilised.

A contacting measurement apparatus may be provided in which the same contact wheel or stationary contactor is used for both transmission and reception of vibrational energy. In one such embodiment, a vibrating contactor in contact with the board product is excited over the predetermined frequency range, and in this respect acts as the contacting transmitter. A receiving transducer, which in an exemplary arrangement is an accelerometer, is associated with the contactor to measure overall vibrational amplitude. In this respect, therefore, the contactor acts as the contacting receiver. According to this embodiment, the overall measured vibrational amplitude represents the response of the board product to the vibrational excitations lying within the predetermined frequency range.

In one preferred embodiment, a single piezo-electric sensor is used in the receiver, and the transmitter includes a vibrating motor, such as a DC motor with a mass eccentrically-mounted on a shaft thereof. Vibrational excitation generated by the motor may be coupled to the board product via a casing of the apparatus. The piezo-electric sensor is preferably mounted in the casing using mechanically isolating, or vibration-damping, components such as elastomer mountings, washers and/or grommets, in order to minimise the direct coupling of vibrational energy from the motor to the sensor via the casing. The sensor may extend through an opening in the casing so as to make contact with the board product, in order to measure the vibrational response of the board product to the excitation generated by the motor. Control of the vibrational frequency may be achieved by controlling a voltage applied to the DC motor. An appropriate contact pressure between the sensor and the board product may be obtained by mounting a suitable weight with the sensor. In this embodiment, the apparatus may advantageously be provided in a compact and portable form.

As will be appreciated, in various alternative embodiments separate transmitter and receiver contactors may be used, and different combinations of contacting and non-contacting transmitters and receivers may be provided.

The processor preferably includes a combination of analogue and/or digital hardware for processing the measured vibrational response to obtain a frequency response of the region of the board product to the vibrational excitation, and for analysing the frequency response to determine a measure of a property of the board product. The processor typically includes a computer including a central processing unit, associated memory, and other peripheral hardware arranged to receive an electrical signal corresponding with the measured vibrational response, wherein the computer is programmed to process and analyse the measured vibrational response.

In some embodiments, the transmitter applies a vibrational excitation having a swept or stepped vibrational frequency, within said predetermined frequency range, and the processor obtains a frequency response by recording the measured vibrational response of the board product corresponding with a series of frequencies within said swept or stepped range.

In alternative embodiments, the transmitter applies a vibrational excitation, such as a white noise type excitation, which simultaneously includes a plurality of frequencies lying within the predetermined frequency range, and the processor obtains a frequency response by recording the measured vibrational response of the board product over a time interval, and computing a corresponding frequency domain response utilising said time response. Computation of the frequency domain response may be performed using a Fourier transformation algorithm, and is most advantageously performed using a Fast Fourier Transform algorithm.

In preferred embodiments, the processor determines a resonant peak frequency of the frequency response within the predetermined frequency range. The processor may apply a scale factor to said resonance peak frequency to compute a measure of board quality. The scale factor may be selected to correspond with the type of board product under test. The processor may compute a value of a property of the board product, such as an MD shear value and/or a shear stiffness value, based upon said resonance peak frequency or said measure of board quality.

In a particular embodiment, the finished board product includes a plurality of components assembled to form a multi-layer product, and the apparatus includes a corresponding plurality of stiffness sensors for estimating the strength of each said component prior to assembly of the product, whereby the processor determines an expected value of the property of the board product based upon said strength estimates, and compares the expected value with the measured value of the property of the finished board products in order to detect damage or degradation of the product during assembly. In one particularly preferred arrangement, the board product is a corrugated paperboard product including first and second outer paper liners and a corrugated paper core sandwiched therebetween, and the apparatus includes corresponding first, second and third stiffness sensors.

Further preferred features and advantages of the present invention will be apparent to those skilled in the art from the following description of preferred embodiments of the invention, which should not be considered to be limiting of the scope of the invention as defined in any of the preceding statements, or in the claims appended hereto.

BRIEF DESCRIPTION OF THE DRAWINGS

Preferred embodiments of the invention are described with reference to the accompanying drawings, wherein like reference numerals refer to like features, and in which.

DETAILED DESCRIPTION OF PREFERRED EMBODIMENTS

Figure 1:
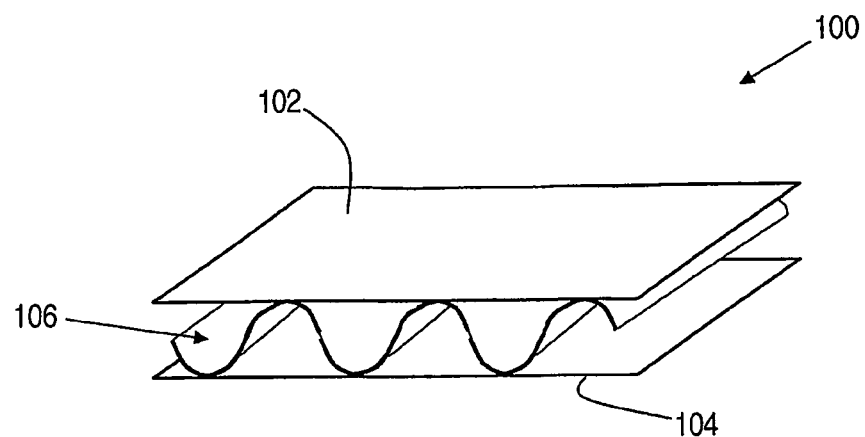
FIG. 1 illustrates the structure of a typical corrugated paperboard product.

Referring firstly to FIG. 1 there is illustrated schematically the structure of a corrugated paperboard product 100. The corrugated paperboard product 100 consists of a top liner or skin 102, a bottom liner or skin 104 and a corrugated fluting or medium 106 sandwiched therebetween. The corrugated paperboard product 100 is typically manufactured from paper, or similar webs of material, and is therefore generally relatively lightweight. However, the provision of corrugated medium 106 results in a product that is extremely strong relative to its weight. Nonetheless, the strength of the board product 100 may be significantly reduced as a result of any damage or degradation caused during the manufacturing process. The present invention is therefore directed to assessing relevant properties of the board product 100, and particularly properties indicative of board strength, during and/or subsequent to manufacture.

Figure 2:
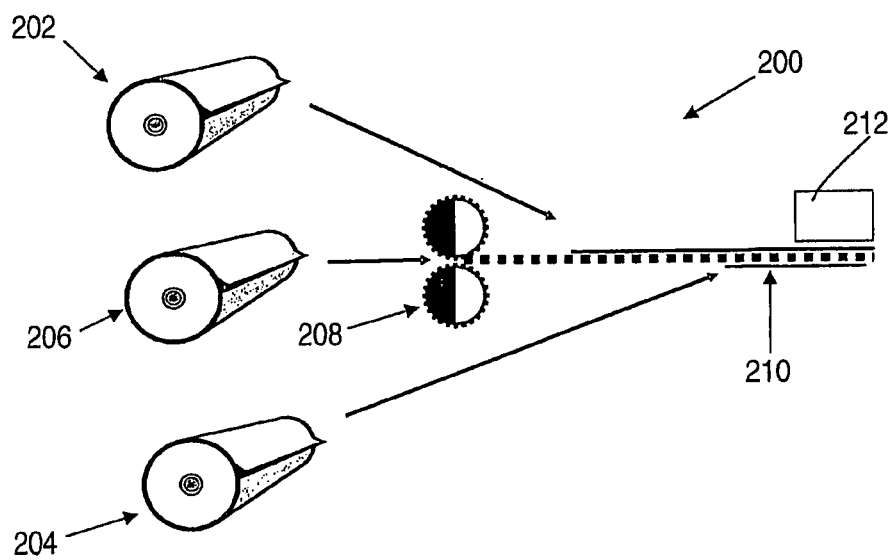
FIG. 2 shows schematically a manufacturing process for a corrugated paperboard product, such as that illustrated in FIG. 1, including on-line measurement of board properties in accordance with the present invention.

FIG. 2 illustrates schematically an arrangement 200 for manufacturing corrugated paperboard such as the exemplary product 100 illustrated in FIG. 1. According to the manufacturing process, the components of the board product, being the rolled webs of material such as paper 202, 204, 206, are continuously dispensed. Paper webs 202, 204 form the top and bottom liners 102, 104 of the finished product respectively. Paper web 206 passes through meshed rollers 208, thereby forming the corrugation which will become the medium 106 of the finished board product. On the production line, the liner webs 202, 204 are fixed to the corrugated medium 206, typically using a suitable adhesive, so as to continuously form the finished corrugated paperboard product 210. This process will be familiar to those skilled in the art, and it will also be appreciated that the finished board product 210 is produced continuously and moves along the production line in the so called machine direction (MD), which is from left to right as illustrated in FIG. 2.

In accordance with some embodiments of the invention, continuous on-line monitoring of board properties, and particularly those properties indicative of board strength, is provided by measuring apparatus 212.

Figure 3:
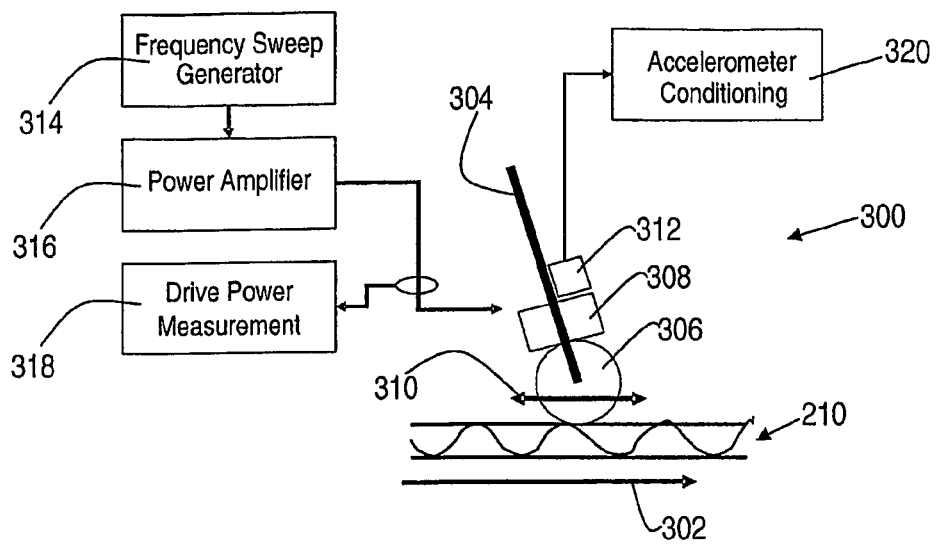
FIG. 3 illustrates schematically an apparatus for measuring machine direction shear strength of a board product according to an embodiment of the invention.

FIG. 3 illustrates an exemplary embodiment 300 of the inventive apparatus 212. As shown, the assembled board product 210 passes under the apparatus in the machine direction, indicated by arrow 302. A support 304 holds the measurement apparatus in contact with the moving board 210, and is arranged so as to apply an appropriate load pressure maintaining the apparatus in contact with the board 210 without applying an excessive force so as to avoid any damage or degradation in board strength.

The apparatus 300 includes a contactor, in the form of rotatable contact wheel 306, which is thereby able to maintain continuous contact with the board 210 as it passes under the apparatus 300 in the machine direction 302. As described in greater detail below, in the embodiment 300 the contact wheel 306 acts as both transmitting contactor and receiving contactor. However, in other embodiments, such as those described later with reference to FIGS. 4 and 5, separate transmitting and receiving contactors may be provided.

The measurement apparatus 300 further includes an actuator 308 which may be, for example, an electromagnetic or mechanical actuator, which generates a vibrational excitation of the apparatus. The direction of the vibrational excitation is preferably selected to exercise a particular desired structural characteristic of the board product 210. Measurement apparatus 300 is designed to measure shear strength of the board product 210, and it is therefore desirable that the vibrational excitation be primarily directed parallel to the machine direction, in an oscillating motion as indicated by the arrow 310 in FIG. 3. However, the structural characteristics of interest may be excited in embodiments of the invention by a variety of different vibrational excitations, applied in other directions.

A receiving transducer 312 is provided, which measures the overall vibrational energy or amplitude of the apparatus. The receiving transducer 312 may be, for example, an accelerometer, a piezo-electric sensor, or similar.

The actuator 308 generates a forced oscillating vibration 310 through contact wheel 306 which is transferred to the moving board product 210. The overall vibration level measured by accelerometer 312 depends upon the structure of the board product 210, which will absorb vibrational energy in a generally frequency-dependent manner, the precise frequency response being determined by properties of the board product 210, such as the shear stiffness of the corrugated medium 106.

Accordingly, in order to obtain a measure of the frequency response of the region of the board product 210 passing under the contact wheel 306, a frequency sweep generator 314 is provided. The frequency sweep generator 314 generates a swept or stepped electrical output covering a plurality of frequencies lying within a predetermined frequency range. As will be described later, with particular reference to FIGS. 6 and 7, a preferred frequency range includes a range of acoustic frequencies, generally being between 50 Hz and 400 Hz, and more particularly between 100 Hz and 300 Hz, however it will be appreciated that a measure of properties of interest may be obtained from analysis of the frequency response of the board product 210 over alternative frequency ranges. In particular, the most appropriate frequency range may depend upon the nature of properties of the particular board product, as well as upon characteristics of the measuring apparatus.

The output of frequency sweep generator 314 is amplified by a power amplifier 316, and used to drive actuator 308 which thereby converts the electrical input signal into a vibrational excitation as previously described. An on-line measurement of the electrical driving power to the actuator 308 is performed using power measurement apparatus 318. The drive power measurement may be used either as a feedback mechanism to power amplifier 316 to ensure that a constant drive power is applied over the complete input frequency range, or alternatively may be used in combination with the measured vibrational response provided by accelerometer 312 to compute the overall vibration levels relative to the input drive power. Whichever approach is adopted, the overall objective is to obtain a measure of the frequency response of the region of the board product 210 under test that is not influenced by any frequency dependent variations in drive power.

The measured vibration level is represented by an electrical output signal generated by the accelerometer (or other sensor) 312. This electrical output signal is processed by the accelerometer conditioning apparatus 320. It will be appreciated that in a practical embodiment of the apparatus 300 depicted schematically in FIG. 3, the overall operation of the measurement apparatus would typically be controlled by an electronic processor including a combination of analogue and/or digital hardware for processing the measured vibrational response to obtain a frequency response of the region of the board product 210 under test, and for analysing the frequency response to determine the desired measure of board properties. In particular, the apparatus may be computer controlled, the controlling computer including a central processing unit and associated memory and other peripheral hardware arranged to receive the electrical signal generated by the accelerometer 312, and also preferably to control the operation of the frequency sweep generator 314. A suitable computer program is thereby able to provide the required control and processing functions.

As will be appreciated from the foregoing description, in the exemplary embodiment 300 a vibrational excitation is applied to a region of the board product 210 having a swept or stepped vibrational frequency within a predetermined frequency range, and a processor obtains the frequency response of the region of the board product 210 by recording the measured vibrational response of the board product corresponding with a series of frequencies within the swept or stepped frequency range. However, it will be appreciated that other methods of excitation and measurement of the frequency response of the region of board product 210 may be employed. For example, in one alternative embodiment a vibrational excitation may be applied, such as a white noise type excitation, which simultaneously includes a plurality of frequencies lying within the predetermined frequency range, whereby the processor obtains the frequency response of the board product 210 by recording the measured vibrational response of the board over a time interval, and computing the frequency response from said time response. In particular, a frequency response may be obtained by computing a Fourier transform of the time response, for example using a Fast Fourier Transform (FFT) algorithm.

Figure 4:
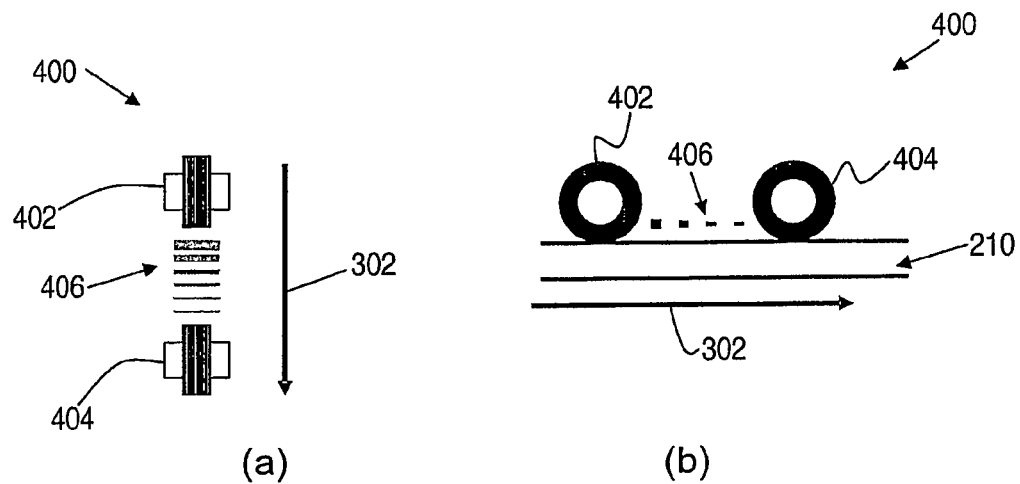
FIG. 4 shows an alternative transmitter and receiver arrangement according to an embodiment of the invention.

FIG. 4 illustrates an alternative arrangement 400 for applying a vibrational excitation to a region of a board product 210 and receiving a measurement of the vibrational response of the board product. In FIG. 4, diagram (a) illustrates a top view of the arrangement, while diagram (b) illustrates a corresponding side view. According to the embodiment 400, a transmitter includes a first contactor in the form of contact wheel 402, and a separate receiver includes a second contactor in the form of contact wheel 404. Vibrational excitations of the region of the board product 210 within which the transmitter 402 and receiver 404 are located are transmitted through the board product as indicated schematically by wavefronts 406. The velocity of the vibrational waves transported through the board product 210, as well as the absorption or attenuation of the vibrational energy within the board product, will be frequency dependent according to the structural properties of the board. Accordingly, by utilising drive and measurement arrangements corresponding with those previously described in relation to FIG. 3, a frequency response of the board product 210 over a predetermined frequency range may be obtained based upon the frequency-dependent vibrational levels detected at the receiver 404 and/or the frequency-dependent propagation delay of the excitations between the transmitter 402 and receiver 404.

Figure 5:
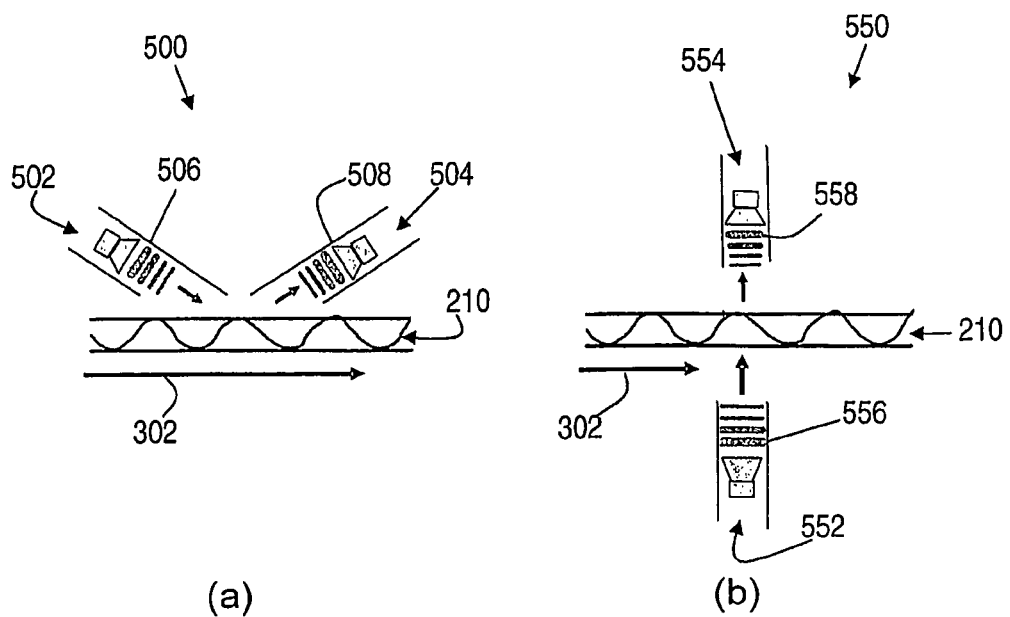
FIG. 5 illustrates a non-contact transmitter and receiver arrangement according to a further embodiment of the invention.

While the embodiments 300, 400 both require contact with the moving board product 210 in order to perform a frequency response measurement, FIG. 5 illustrates alternative non-contact embodiments 500, 550. In the non-contact embodiments shown, a vibrational excitation is provided to a region of the board product 210 using non-contacting transmitters 502, 552 to apply a vibrational excitation via soundwaves. The non-contacting transmitters 502, 552 typically include a transducer having an amplifier and speaker, which is directed towards the region of the board product 210 under test.

The sound waves generated by transmitters 502, 552 generate corresponding vibrational excitations within the board product 210, which are re-emitted and detected using non-contacting receivers 504, 554, which receive soundwaves emitted from the region of the board product 210 under test. Suitable receivers 504, 554 include microphones, such as directional microphones directed towards the corresponding region of the board product 210.

In order to direct the output soundwaves to the desired region of the board product 210, acoustic waveguides 506, 556 may be associated with the transmitters 502, 552. Similarly, in order to focus the received soundwaves from the intended region of the board product 210, further acoustic waveguides 508, 558 may be associated with receivers 504, 554.

In the non-contact embodiment 500, the soundwaves are directed onto a top surface of the board product 210 at an appropriate angle, and the receiver 504 measures the soundwaves re-emitted from the same surface at a corresponding angle. Accordingly, embodiment 500 operates effectively in a reflection mode. By comparison, alternative non-contacting embodiment 550 directs soundwaves into a lower surface of the board product 210, and receives soundwaves re-emitted from the opposing surface. Accordingly, the embodiment 550 operates effectively in a transmission or absorption mode. While both embodiments 500, 550 may provide a practical arrangement for measuring a frequency response of the board product 210, the embodiment 500 is advantageous when it is more convenient to provide access to the board product from only one side. In particular, an arrangement such as that of embodiment 500 may enable the development of a practical non-contacting handheld testing device for performing spot measurements of the properties of board products.

Figure 6:
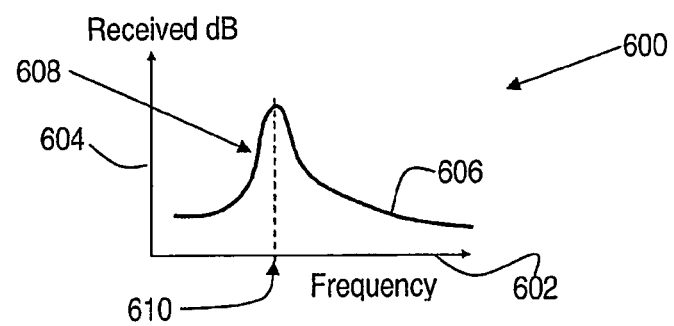
FIG. 6 is a schematic illustration of a typical frequency response of a board product measured in accordance with embodiments of the invention.
Figure 7:
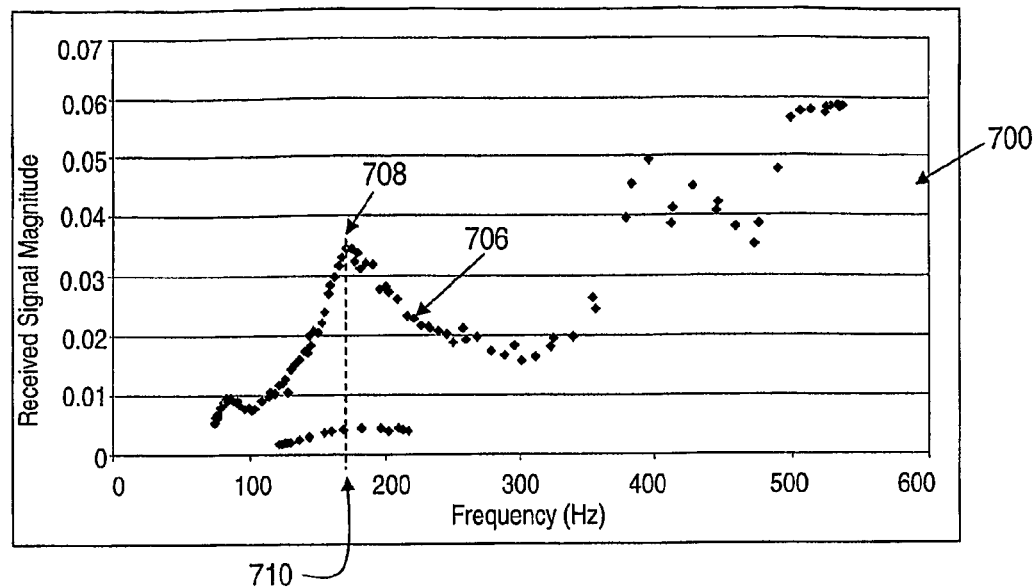
FIG. 7 shows an exemplary measured frequency response according to an embodiment of the invention.

FIG. 6 illustrates schematically a typical vibrational frequency response 600 such as would be measured over a suitable frequency range by various embodiments of the invention, including those previously described with reference to FIGS. 3 to 5. The x-axis 602 of graph 600 represents frequency, while the y-axis 604 represents the received vibrational power or energy, represented for example in decibels. The overall response 606 includes a resonant peak 608 occurring at resonance peak frequency 610. The frequency response 606 includes a great deal of information regarding the properties of the board products under test, and analysis of the frequency response may therefore be performed to obtain a measure of at least one such property of the board product.

In particular, experiments and analysis by the present inventors have established a correspondence between the resonance peak frequency 610 and the MD shear stiffness of a board product. The resonant peak 608 associated with shear stiffness has been found to lie within an acoustic frequency range, as illustrated by the graph 700 in FIG. 7, which depicts an exemplary frequency response measured in accordance with an embodiment of the invention. Specifically, the measured response 706 includes a clear resonant peak 708 which has been identified by obtaining a frequency response over an acoustic frequency range lying generally between 50 Hz and 400 Hz and more specifically between 100 Hz and 300 Hz, which represent adjacent minima of the frequency response 706. The resonant peak 708 occurs at a corresponding resonance peak frequency 710, which is approximately 175 Hz in the example 700.

As previously discussed, it is believed that the resonance peak frequency 608, 708 is related to the shear stiffness of the board product, which is known to correspond with board strength. In particular, a stiffer, and thus stronger board product exhibits a higher resonance peak frequency 610, 710 than a less stiff, and thus less strong, product. It is therefore proposed in accordance with the invention that analysis of the frequency response 606, 706 may be utilised in a variety of ways to determine properties of interest of a board product under test. For example, it may be possible to determine intrinsic properties of a board product, such as shear stiffness, directly from measurement of the resonance peak frequency 610, 710. Alternatively, continuous measurement on a board product during manufacture may enable damage or degradation to be detected in relative terms, whereby a shift in the resonance peak frequency 610, 710 from higher to lower frequencies is indicative of a reduction in shear stiffness, and therefore strength, of the manufactured board product.

Furthermore, it is envisaged that embodiments of the present invention may provide an alternative to the known twisting test method for shear stiffness, with the further advantages of being non-destructive of the board product under test, and being capable of use in a continuous on-line manner. Accordingly, comparisons have been conducted between measurements of the resonance peak frequency of samples of various board products in accordance with embodiments of the present invention, and measurements of MD shear of the same samples utilising the prior art twisting test method. Results of these comparative measurements are illustrated in the graph 800 shown in FIG. 8. Three sets of measurements are shown, corresponding with comparative tests on samples of B-flute, C-flute and Xitex™ board products, which have been subjected to various degrees of damage or degradation. (As will be known to those skilled in the art, Xitex™ is a double-wall corrugated board product manufactured by Amcor Limited, which is composed of a "back-to-back" combination of B- and C-flutes.)

In the graph 800 the open circles and line 802 represent the comparative measurements of B-flute product, the open squares and line 804 represent the comparative measurements of C-flute products, and the open triangles and line 806 represent comparative measurements of Xitex™ products. The x-axis 808 represents the measured value of MD shear according to the twisting test method, while the y-axis 810 represents the resonance peak frequency measured in accordance with an embodiment of the present invention. It is evident that a strong linear correlation exists in each case between the prior art MD shear values and the resonance peak frequency values. It is thus anticipated that measurements performed in accordance with embodiments of the present invention not only provide a useful alternative to the conventional MD shear twisting test measurements, but with appropriate calibration may provide a measure of shear stiffness and strength properties of board products corresponding with the familiar MD shear values to which existing manufacturers of board products have become accustomed. In other words, embodiments of the present invention may provide a direct substitute for the prior art twisting test, which also enables on-line continuous measurement of shear stiffness in a non-destructive manner.

Figure 9:
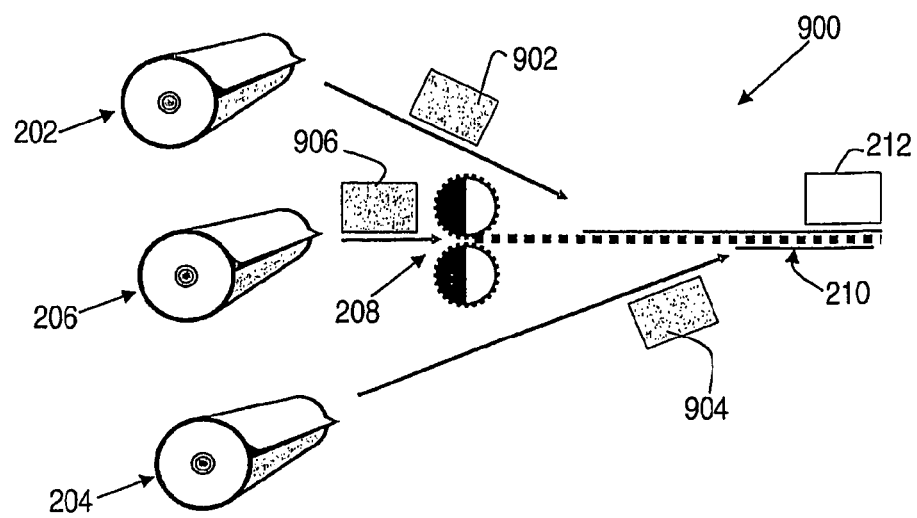
FIG. 9 illustrates an arrangement for on-line measurement of board properties along with strength of board components according to an embodiment of the invention.

FIG. 9 illustrates a further arrangement according to an embodiment of the present invention in which an on-line measurement of board properties is performed by apparatus 212 in combination with on-line estimation of the strength of individual board components. In the exemplary arrangement 900 shown in FIG. 9, the three paper web components 202, 204, 206 of the finished board product 210 are subject to continuous on-line stiffness measurement using the corresponding stiffness sensors, 902, 904, 906. The resulting stiffness measurements may be used to estimate the strength of each component. It is envisaged that by estimating strength data corresponding with the component parts of the finished board product 210 to the processor controlling on-line measurement of board properties it is possible to compute an expected value of the properties of interest of the finished board product. For example, knowing the estimated strength of the component materials, 202, 204, 206 an expected value of the shear stiffness of finished board product 210 may be computed, and compared with the measured value obtained using the measurement apparatus 212. Comparison of the expected and measured values may be used to detect damage or degradation of the product which may have occurred during manufacture.

Figure 10:
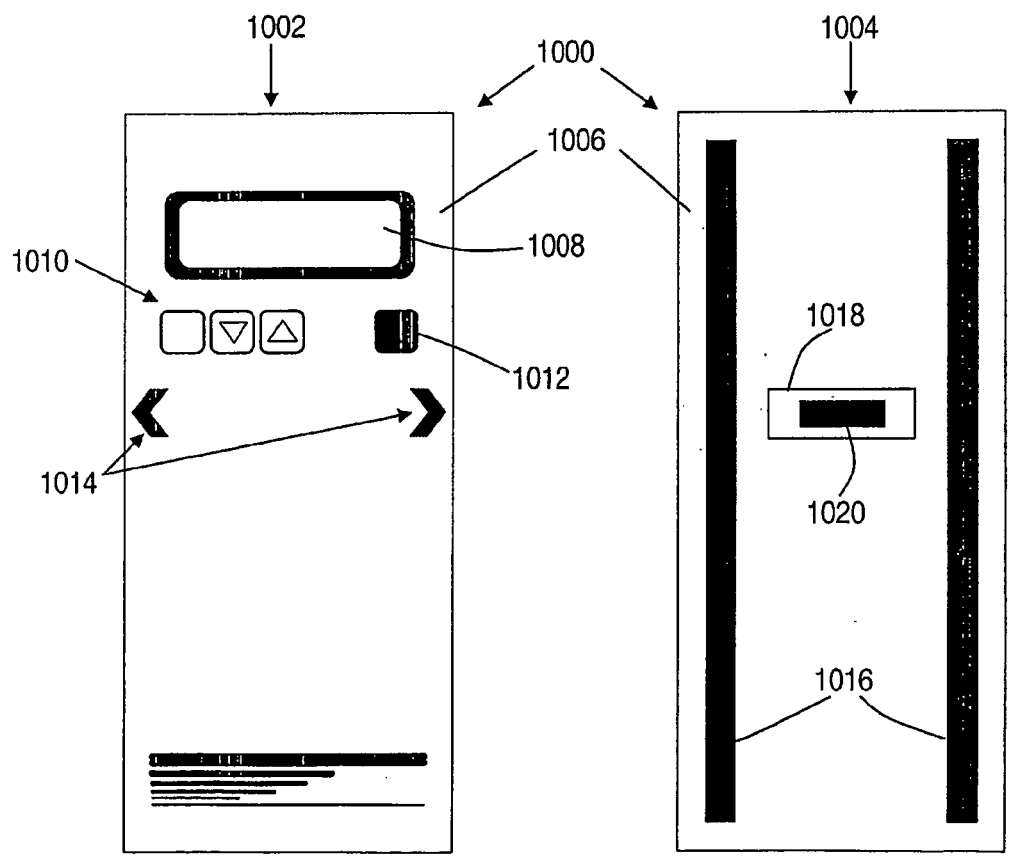
FIG. 10 illustrates top and bottom views of a portable apparatus for measuring board properties according to an embodiment of the invention.

In a further embodiment of the invention, a portable apparatus for measuring board properties is provided. External views of the portable apparatus 1000 are illustrated in FIG. 10, which includes a top view 1002 and a bottom view 1004. The components of the portable apparatus 1000 are all enclosed within a casing 1006, preferably made from aluminium, steel or other suitable rigid material.

On the top face 1002 of the portable measurement apparatus 1000 there is provided a user interface including a display 1008, configuration controls 1010, a measurement initiation control 1012, and guide markings 1014. According to the presently preferred embodiment, the display 1008 is a conventional liquid crystal display unit. The configuration controls 1010 consist of three buttons, which together enable the user to scroll through and select various options and settings presented on the display 1008. The configuration controls 1010 also enable the user to change configuration settings that have been selected. Some of the configuration options that may be accessed using the configuration controls 1010 will become apparent from the following more detailed description of the operation of the portable measuring apparatus 1000.

The measurement initiation control 1012 is a button which, when pressed, causes the portable unit 1000 to commence a measurement of board properties. The guide indicators 1014 are markings on the top panel 1002 of the portable apparatus 1000 which assist a user in aligning the receiving sensor 1020 projecting from the opposing side of the measurement unit 1000, as described in greater detail in the following paragraphs. The preferred embodiment of the portable measurement apparatus 1000 includes two rests 1016, in the form of rubber strips, which are affixed to the bottom face 1004 of the casing 1006. An opening 1018 formed in the bottom face 1004 enables an internally-mounted receiving sensor 1020 to project through the casing 1006, in order to make contact with a board product under test. The mounting arrangement of the receiving sensor 1020 is described in greater detail below with reference to FIG. 12.

Figure 11:
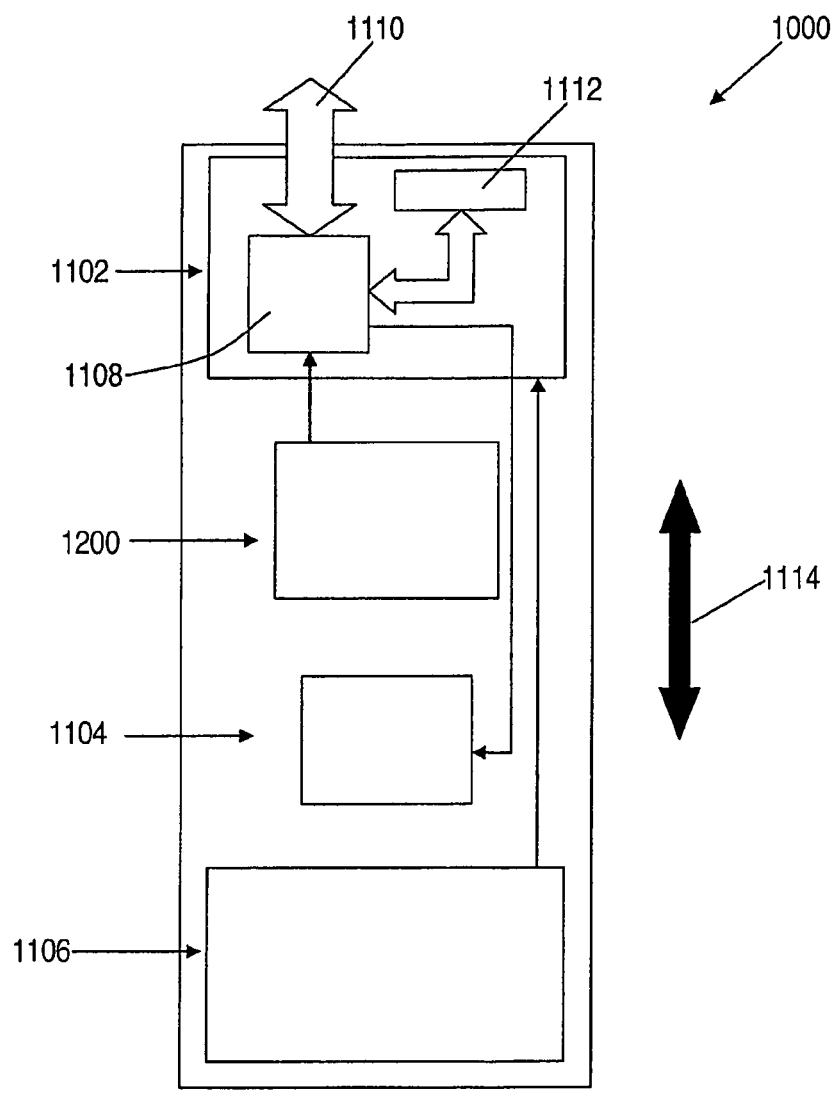
FIG. 11 is a block diagram illustrating schematically the major components of the portable apparatus for measuring board properties.

FIG. 11 is a block diagram which illustrates schematically a number of major components of the portable measurement apparatus 1000. The apparatus 1000 includes an electronic processing unit 1102, a receiver 1200, a transmitter 1104, and an internal power source, in the form of a rechargeable battery 1106.

In the presently preferred embodiment, the electronic processing unit 1102 consists principally of an electronic circuit board upon which are mounted various digital and analog electronic components for implementing the major processing functions of the portable measurement apparatus 1000. In particular, the electronic processing unit 1102 includes a microprocessor or microcontroller 1108. The microprocessor 1108 is operatively coupled to a storage medium, which preferably includes a non-volatile memory device which permanently contains program instructions for execution by the processor 1108. Volatile storage, such as random access memory, for the temporary storage of program variables, data and so forth, may also be provided. As will be appreciated, numerous implementations of the electronic processing unit 1102 are possible, according to which the required storage media may be provided in different forms. For example, according to one particularly convenient implementation the microprocessor 1108 is a microcontroller device which includes internally all of the required volatile and non-volatile storage, along with various additional peripheral devices for facilitating interfaces with the receiver 1200, transmitter 1104, and other components of the portable apparatus 1000. Alternatively, a basic microprocessor may be utilised in combination with a number of external storage devices and/or peripheral interfaces. Since these various design and implementation options will be readily apparent to those skilled in the art of electronic circuit design, they will not be discussed in detail herein, and for simplicity details of the storage and peripheral devices are omitted from the drawings.

An interface 1110 is provided between the microcontroller 1108 and the top panel user interface components such as the display 1008, the configuration controls 1010 and the measurement initiation control 1012. A user is thereby enabled to interact with, configure and control the operation of the measurement apparatus 1000 implemented via the microcontroller 1108. Additionally, in the presently preferred embodiment of the apparatus 1000 an external serial interface 1112 is also provided. The serial interface 1112 enables the apparatus 1000 to be connected to external devices, such as a printer or a computer terminal such as a PC. For example, by connecting the apparatus 1000 to a printer, hardcopy of measurement results may readily be generated. Connection to an external computer terminal may enable the portable apparatus 1000 to be automatically operated under computer control. For example, in one such application an external computer-controlled system may be used to automatically position the apparatus 1000 at different locations on a board product under test, wherein the controlling computer is able to initiate measurements and receive measurement results via the serial interface 1112, without the need for ongoing operator intervention.

In the presently preferred embodiment, the transmitter 1104 includes a vibrating motor, which is a DC electric motor having a shaft with a mass eccentrically mounted thereon. A voltage applied to the vibrating motor determines the speed of rotation of the shaft, ie the frequency of operation. The eccentrically-mounted mass thus generates vibrations along a direction substantially perpendicular to the motor shaft, the vibrations having a frequency corresponding with the rotation frequency of the motor. In the presently preferred embodiment of the apparatus 1000 the motor shaft is oriented such that its axis is directed across the short dimension of the casing 1006, ie from left to right as shown in FIGS. 10 and 11. Further, the motor is securely fixed to the casing 1006 such that the entire casing 1006 is caused to vibrate. The predominant direction of oscillation is along the long dimension of the casing 1006, ie from top to bottom as illustrated in the drawings, and as indicated by the double-headed arrow 1114 in FIGS. 11 and 13.

The microcontroller 1108 controls the frequency of vibration by applying a corresponding voltage to the motor 1104. Each voltage applied to the motor 1104 is represented internally to the microcontroller 1108 by a corresponding digital value. As will be appreciated, the conversion of the internal digital value to the controlling voltage is readily achieved using a digital-to-analog converter, which may be integrated with, or external to, the microcontroller 1108, along with suitable buffering and/or amplifying analog circuitry for converting the output analog value to an appropriate driving voltage for the motor 1104. In particular, according to the presently preferred embodiment, the microcontroller 1108 is programmed to perform a measurement in which a series of stepped vibrational frequencies is generated by stepping through a number of corresponding digital control values. The corresponding response of a board product under test to each frequency in the series, which covers a predetermined frequency range, is then measured using the receiver 1200. The microcontroller 1108 is thus able to measure the overall frequency response of the board product under test over the predetermined frequency range, in the manner previously described generally with reference to FIGS. 6 to 8.

Figure 12:
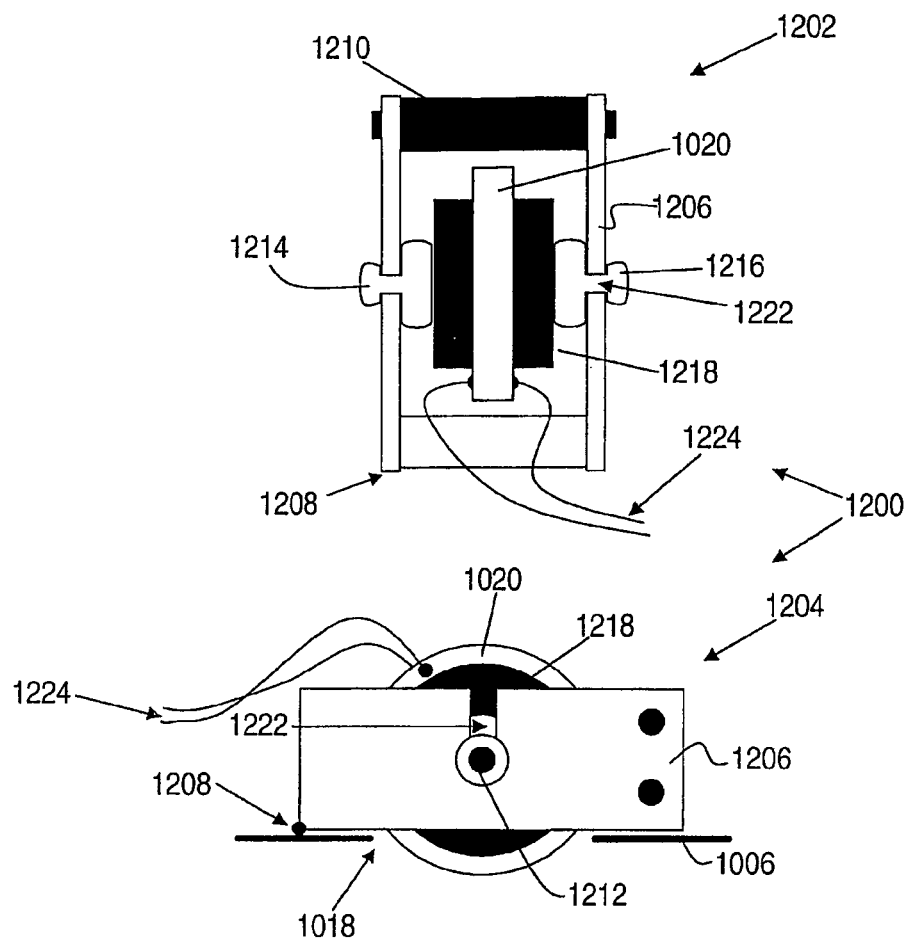
FIG. 12 shows top and side views of a vibration sensor for use in the portable apparatus for measuring board properties.

Details of the receiver employed in the presently preferred embodiment of the portable apparatus 1000 are shown in FIG. 12. In particular, a top view 1202 and a corresponding side view 1204 of the receiver 1200 are illustrated in the drawing. It will be understood that the primary function of the receiver is to detect the amplitude of vibrations in a board product under test, which has been vibrationally excited via the casing 1006 of the portable apparatus 1000, as a result of operation of the transmitting motor 1104. It is therefore necessary that the receiving sensor 1020 is, as far as practicable, isolated from the influence of vibrations directly transferred from the motor 1104 via the casing 1006, since such direct vibrations will tend to mask the measurements of vibrations transferred via the board product under test. The mounting arrangements of the receiver 1200, as illustrated in FIG. 12, are designed to achieve a sufficient degree of isolation between the vibrating motor 1104 and the receiving sensor 1020.

The receiver 1200 includes a rigid mounting unit 1206, which may be made from any suitable rigid material, such as aluminium. When mounted within the casing 1006 the rigid mounting unit 1206 is hinged at one edge 1208 thereof. Any suitable hinging mechanism may be utilised, and according to a particularly straightforward arrangement the mounting unit 1206 is simply adhered to a flexible material which is itself partially adhered on its opposing side to the casing 1006. Accordingly, the hinging is achieved simply as a result of the flexibility of the connecting material.

At the end of the mounting unit 1206 opposed to the hinge point 1208, there is provided a deadweight 1210. Accordingly, in use a corresponding downward force is applied, which will act to maintain an appropriate level of contact between the receiving sensor 1020 and a board product under test.

A shaft 1212 extends across the mounting unit 1206. Snugly fitted onto the shaft is an elastomer ring 1218, at either side of which are mounted further elastomer grommets 1214, 1216. A piezo-electric ring sensor 1020 is fitted over the elastomer ring 1218, and is preferably adhered thereto. The elastomer grommets 1214, 1216 are fitted snugly into corresponding recesses 1220, 1222 formed in the mounting unit 1206. Conductive wires 1224 are soldered to opposing contacts of the piezo-electric ring sensor 1020 whereby detected vibrations are transmitted back to the electronic processing unit 1102, where they may be converted into digital form, eg using suitable conditioning circuitry and an analog-to-digital converter, for processing within the microcontroller 1108.

The attachment of the mounting unit 1206 via a hinge 1208, in combination with the vibration-damping elastomer grommets 1214, 1216 and ring mounting 1218, together serve to provide a high degree of mechanical isolation of the piezoelectric ring sensor 1020 from the casing 1006 of the portable apparatus 1000. Accordingly, in use vibrations received and converted into electrical form by the piezo-electric ring sensor 1020 are predominantly those that are transmitted via the board product under test.

Figure 13:
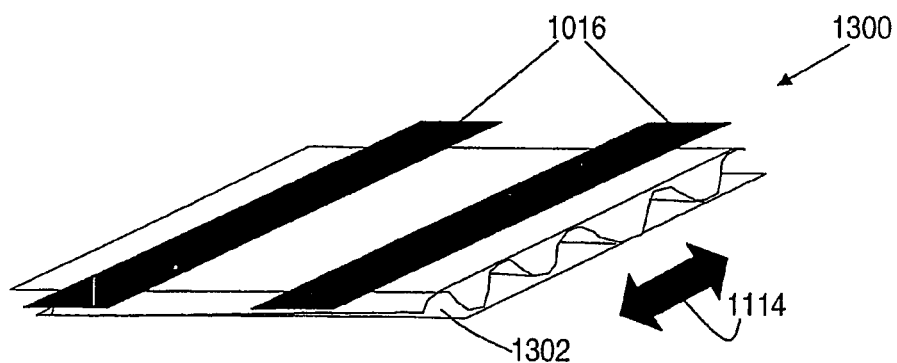
FIG. 13 is a schematic illustration indicating a preferred operating orientation of the portable apparatus for measuring board properties, relative to a board product under test.

FIG. 13 illustrates schematically an arrangement 1300 that is preferably used for performing measurements on a static board product 1302. The portable apparatus 1000 is rested on the board product 1302 under its own weight, an is oriented such that the rubber rests 1016 lie perpendicular to the direction of the flutes of the board product 1302. In operation, vibrations generated by the vibrating motor 1104 are transferred via the casing 1006 and rubber rests 1016 to generate vibrations in the board product 1302 that are predominantly directed perpendicular to the flute direction. As previously described generally with reference to FIGS. 1 to 8, this arrangement thereby enables vibration measurements to be performed that correspond with shear testing measurements along the machine direction of a typical production line. Accordingly, the portable apparatus 1000 may be used for random or spot tests of manufactured board products, utilising a simple and non-destructive procedure.

Figure 14:
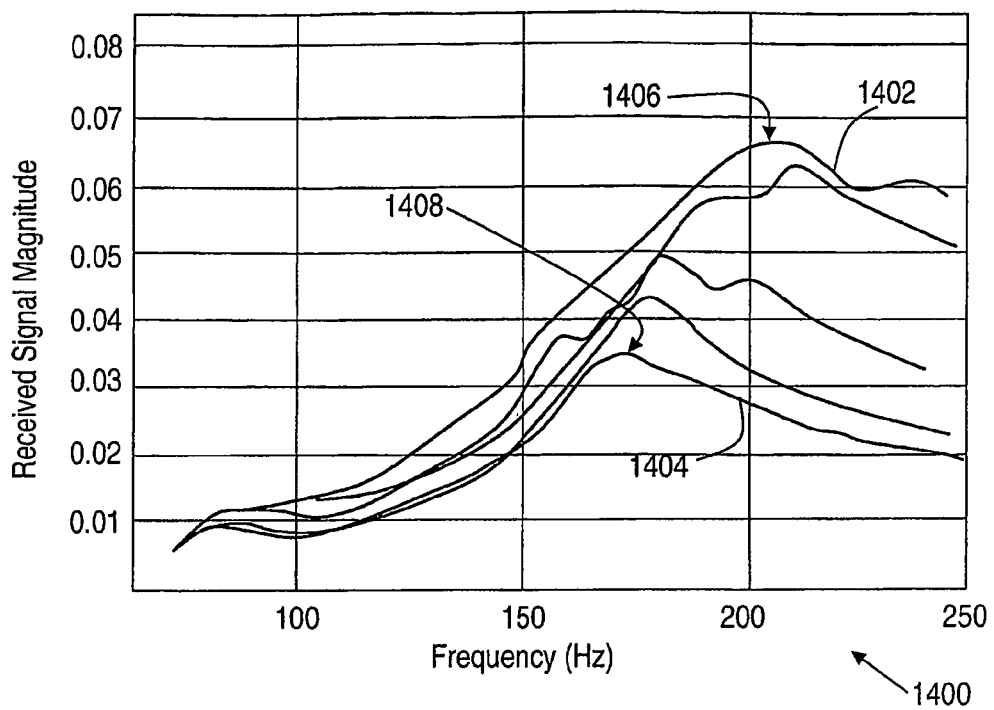
FIG. 14 is a graph showing exemplary measured frequency response data obtained using the portable apparatus for measuring board properties.

FIG. 14 shows a graph 1400 including a number of frequency response measurements performed using a presently preferred embodiment of the portable apparatus 1000. The sequence of frequency response curves ranging from the top curve 1402 to the bottom curve 1404 represent measurements performed on a sample having increasing degrees of damage applied. As can be seen, the peak resonance frequency shifts from a higher value 1406 to a lower value 1408 as the level of damage increases, corresponding with a decrease in board quality and strength.

Figure 15:
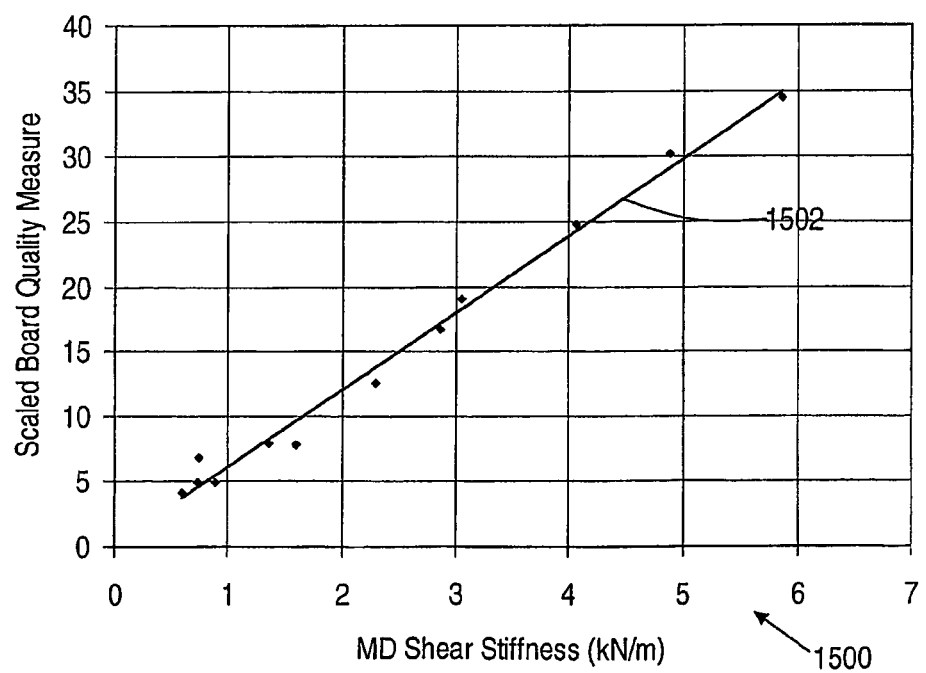
FIG. 15 illustrates a linear relationship between a resonant peak frequency measured using the portable apparatus for measuring board properties, and a measurement of MD shear using the prior art twisting test method.

FIG. 15 shows a graph 1500 including the line 1502 that is obtained by plotting measurements obtained using the portable apparatus 1000 against corresponding measurements of MD shear made using the prior art twisting test method. Similarly with the results shown in FIG. 8, a substantially linear relationship is demonstrated.

Figure 8:
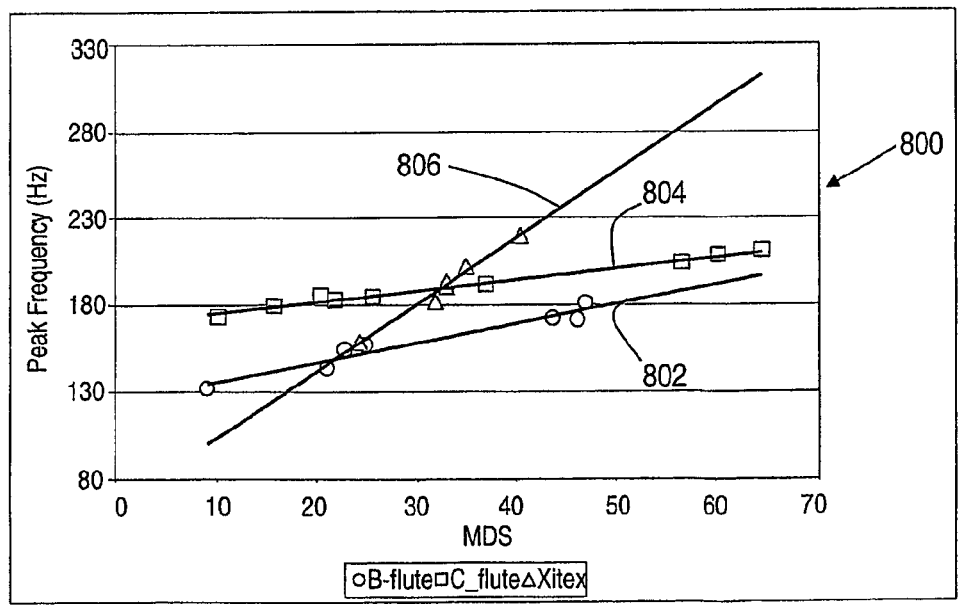
FIG. 8 illustrates a linear relationship between a resonance peak frequency measured according to an embodiment of the invention, and a measurement of MD shear made using the prior art twisting test method.

As the various test results illustrated in FIGS. 8 and 15 demonstrate, for any given board product there is a strong linear correlation between measured peak resonance frequency and MD shear stiffness. However, the exact values of peak frequency may depend upon a particular measurement apparatus, for example due to mechanical coupling effects, and are not generally independently physically meaningful in their own right. That is, in the absence of a pre-calibrated known relationship between the measured resonance peak frequency and corresponding shear stiffness for a given type of board product, the peak frequency itself is generally arbitrary and of no particular interest to the end user. Accordingly, it is presently preferred to employ a suitable calibration and scaling technique resulting in a relative measure of board quality, which is adjusted to have a magnitude generally convenient to end users. In particular, by multiplying a measured peak frequency value by a suitable scale factor, which may be selected to correspond with a particular type of board product under test, a relative board quality measure may be obtained that is suitable for presentation to the user, for example via the display 1008 of the portable apparatus 1000.

In accordance with a particularly preferred approach, the user is able to identify the type of board product under test using the configuration controls 1010, and the microcontroller 1108 is programmed to select an appropriate scale factor based upon the specified product type. In this way, despite the differing linear relationships existing between the peak frequency value and corresponding MD shear for different types of board, as illustrated in FIG. 8, a board quality measure value can be provided to the user that is directly comparable across different types of board products. It is presently considered most convenient to provide board quality measure values lying within the range of zero to 100. However, it will be appreciated that this selection of scale factor is arbitrary, and alternative scalings may be utilised. In particular, the measured resonance frequency, and hence the scaled board quality measure values, are generally proportional to board stiffness, and it may be desirable in some embodiments to provide apparatus which outputs measurement results in the form of corresponding MD shear values expressed in standard units.

The presently preferred implementation utilises board quality measure values which, while arbitrary, are directly comparable across measurements thereby enabling the relative quality of different board samples to be compared. This is particularly useful for measuring variations in quality across different locations on a single board sample, comparing the quality of board samples taken from different locations and/or times in a production run, or for measuring the variation in board quality of a single board product over time when subject to various forms of wear and tear.

Figure 16:
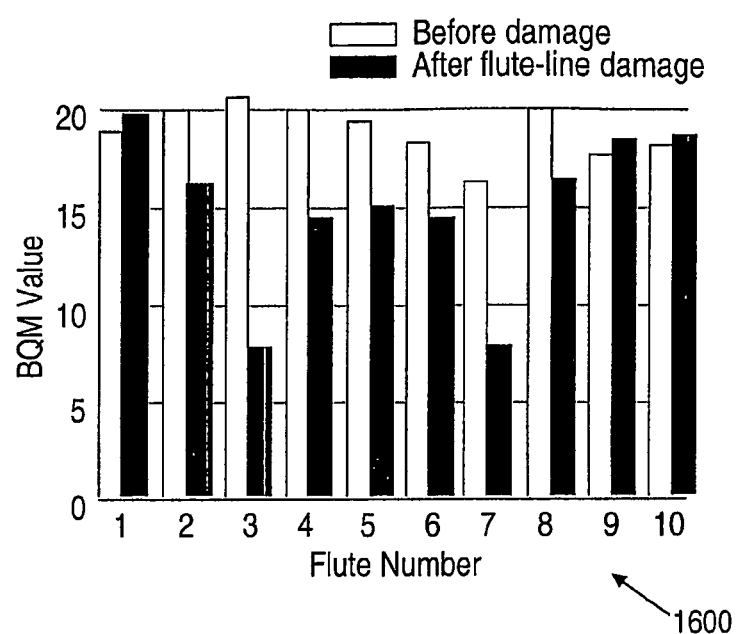
FIG. 16 is a bar chart illustrating measurements of the impact of individual flute-line damage on board properties.

A further advantage of the present invention, in at least preferred embodiments, is the ability to perform measurements having improved spatial resolution as compared with prior art methods. Specifically, the portable measurement apparatus 1000 is capable of measuring the board quality in a localised region having dimensions on the order of 10 mm. For example, FIG. 16 shows a bar chart 1600 illustrating the impact of individual flute-line damage on board properties. Measurements of board quality were made across a board sample, at locations corresponding with a series of ten adjacent flutes, numbered '1' to '10' along the x-axis of the chart 1600, both before and after the intentional introduction of damage to two particular flute-lines, namely those numbered '3' and '7'. The white bars represent the measured quality values before damage, while the black bars are the corresponding measurements subsequent to damage. The ability of the apparatus 1000 to isolate the quality reduction, corresponding with a local reduction in board stiffness associated with the damaged flute-lines, is plainly evident in the chart 1600 by the substantial decrease in the board quality measure recorded in the vicinity of flute numbers '3' and '7' after damage. Prior art methods are generally unable to achieve a spatial resolution of less than 100 mm, which is far greater than the width of individual flutes.

Accordingly, embodiments of the present invention may be used to measure the impact on board quality and strength of processes, such as printing onto the surface of manufactured board products, that may result in highly localised crushing of flutes, or other local damage. Such measurements are generally impossible with existing methods providing a lower spatial resolution.

As will be appreciated from the foregoing discussion, some embodiments of the present invention enable the continuous on-line measurement of properties of manufactured paperboard products, which may be used to provide real-time feedback on production line performance for quality control purposes. Accordingly, lighter grade materials may be employed in the manufacture of paperboard products than is presently the case, since margins required to account for possible undetected damage or degradation during manufacture may be reduced.

Furthermore, other embodiments of the invention have been described which are applicable to assessing the corresponding properties of completed, stationary samples of board products. For such applications, either non-contacting or stationary contacting transmitters and receivers may be employed, and in particular a portable handheld embodiment of the invention has been described which utilises a casing thereof as a contacting transmission medium, and a suitably-mounted contacting piezo-electric receiver.

Additionally, it will be readily apparent to those skilled in the art that many further variations of the present invention are possible, including various combinations of contacting and non-contacting transmitters and receivers, and alternative arrangements for the generation, detection and analysis of vibrational excitations. Accordingly, it will be understood that the invention is not limited to the particular embodiments described herein, but rather the scope of the invention is defined by the claims appended hereto.

The invention claimed is:

1. A method of measuring at least one property of a paperboard product, the method comprising:
  applying, by a device, a vibration to a member that applies a vibrational excitation that applies a plurality of frequencies to at least one region of the paperboard product as the paperboard product moves in a machine direction (MD);
  measuring, by the device, a frequency response of the at least one region of the paperboard product to the vibrational excitation;
  determining, by the device, information associated with one or more amplitudes with respect to the frequency response, the one or more amplitudes being associated with one or more vibrations;
  using, by the device, the determined information, associated with the one or more amplitudes with respect to the frequency response, to obtain a measure of the at least one property of the paperboard product; and
  scaling, by the device, the obtained measure of the at least one property of the paperboard product to determine information associated with a quality of the paperboard product.

2. The method of claim 1, where the plurality of frequencies include a range of acoustic frequencies.

3. The method of claim 1, where applying the vibrational excitation includes applying at least one of a swept or stepped vibrational frequency within a range of the plurality of frequencies.

4. The method of claim 1, where the plurality of frequencies are between 50 Hertz (Hz) and 400 Hz.

5. The method of claim 1, where the measure of the at least one property of the paperboard product includes a resonance peak frequency of the measured frequency response within a range of the plurality of frequencies.

6. The method of claim 5, further comprising:
  scaling the resonance peak frequency to provide a measure of paperboard quality.

7. The method of claim 5, further comprising:
  computing, from the resonance peak frequency, a corresponding machine direction (MD) shear value, a shear stiffness value, or a shear modulus value.

8. The method of claim 1, further comprising:
  repeating the applying, measuring, and analyzing at different times or at different locations on the paperboard product, and
  comparing the resulting measures of the at least one property of the paperboard product in order to determine relative differences in paperboard quality at the different times or the different locations.

9. The method of claim 1, where the paperboard product includes a plurality of components assembled to form a multilayer product, and the method further comprises:
  estimating a strength of each component of the paperboard product prior to manufacture of the paperboard product;
  determining an expected value of a property of the paperboard product based upon the strength estimates,
    where applying the vibrational excitation occurs after the manufacture of the paperboard product; and
  comparing the expected value with the measure of the at least one property of the paperboard product in order to detect damage or degradation of the paperboard product during the manufacture of the paperboard product.

10. The method of claim 1, where the vibrational excitation is applied predominantly along a machine direction of the paperboard product.

11. An apparatus for measuring at least one property of a paperboard product, the apparatus comprising:
  a transmitter to apply a vibrational excitation that applies a plurality of frequencies to at least one region of the paperboard product as the paperboard product moves in a machine direction (MD);
  a receiver to measure a vibrational response of the paperboard product to the vibrational excitation; and
  a processor to:
    process the measured vibrational response to obtain a frequency response of the at least one region of the paperboard product to the vibrational excitation,
    determine information associated with one or more amplitudes with respect to the obtained frequency response, the one or more amplitudes being associated with one or more vibrations;
    use the determined information, associated with the one or more amplitudes with respect to the frequency response, to determine a measure of the at least one property of the paperboard product, and
    scale the determined measure of the at least one property of the paperboard product to determine information associated with a quality of the paperboard product.

12. The apparatus of claim 11, where the transmitter includes an electromechanical transducer to convert an input electrical signal into a corresponding vibrational excitation signal.

13. The apparatus of claim 11, where the transmitter includes a contacting transmitter, and where the contacting transmitter is to apply the vibrational excitation.

14. The apparatus of claim 13, where the transmitter includes a transmitting transducer with an actuator to apply vibrational energy to the contacting transmitter to cause the vibrational excitation.

15. The apparatus of claim 14, where the actuator includes a piezoelectric actuator.

16. The apparatus of claim 14, where the actuator includes a vibrating motor.

17. The apparatus of claim 11, where the transmitter includes a non-contacting transmitter.

18. The apparatus of claim 11, where the receiver includes an electromechanical transducer to convert received vibrational energy, associated with the measured vibrational response, into a corresponding output electrical signal that is used by the processor to obtain the frequency response.

19. The apparatus of claim 11, where the receiver includes a contacting receiver.

20. The apparatus of claim 19, where the contacting receiver includes a receiving transducer with a vibration sensor.

21. The apparatus of claim 20, where the vibration sensor includes a piezo-electric sensor.

22. The apparatus of claim 11, where the transmitter, when applying the vibrational excitation, is further to apply a swept or stepped vibrational frequency within a range of the plurality of frequencies, and the processor, when processing the measured vibrational response to obtain the frequency response, is further to record the measured vibrational response of the paperboard product corresponding with the plurality of frequencies within the range of the plurality of frequencies.

23. The apparatus of claim 11, where the processor is further to determine a resonant peak frequency, of the frequency response, within a range of the plurality of frequencies.

24. The apparatus of claim 23, where the processor is further to apply a scale factor to the resonance peak frequency in order to compute a measure of paperboard quality.

25. The apparatus of claim 24, where the processor is further to compute a value of a property of the paperboard product relating to shear stiffness of the paperboard product, based upon at least one of the resonance peak frequency or the measure of paperboard quality.

26. The apparatus of claim 11, where the processor is further to control the transmitter to apply the vibrational excitation, including the plurality of frequencies within a range of the plurality of frequencies, to the at least one region of the paperboard product.

27. An apparatus for measuring at least one property of a paperboard product, the apparatus comprising:
- a transmitting transducer that includes an electrical input, the transmitting transducer being to generate a vibrational excitation that applies a plurality of frequencies determined by an applied electrical input signal;
- a receiving transducer that includes an electrical output, the receiving transducer being to generate an electrical output signal corresponding with an applied vibrational excitation;
- at least one processor;
- at least one storage medium operatively coupled to the at least one processor;
- an output peripheral interface between the at least one processor and the electrical input of the transmitting transducer; and
- an input peripheral interface between the electrical output of the receiving transducer and the at least one processor, the storage medium including one or more instructions for execution by the at least one processor, and execution of the one or more instructions causing the at least one processor to:
  - direct the transmitting transducer to apply the vibrational excitation that simultaneously applies a plurality of frequencies to at least one region of the paperboard product as the paperboard product moves in a machine direction (MD);
  - measure a frequency response of the at least one region of the paperboard product to the vibrational excitation, based on receipt of electrical signals from the receiving transducer corresponding with vibrational excitations received from the paperboard product based on the applied vibrational excitation;
  - determine information associated with one or more amplitudes with respect to the frequency response, the one or more amplitudes being associated with one or more vibrations;
  - use the determined information, associated with the one or more amplitudes with respect to the frequency response, to obtain a measure of the at least one property of the paperboard product; and
  - scale the determined measure of the at least one property of the paperboard product to determine information associated with a quality of the paperboard product.

* * * * *